United States Patent [19]

Ganellin et al.

[11] Patent Number: 4,558,128
[45] Date of Patent: Dec. 10, 1985

[54] 2-SUBSTITUTED ALKYLAMINOPYRIMIDONES

[75] Inventors: Charon R. Ganellin, Welwyn; Robert J. Ife, Stevenage; David A. A. Owen, Welwyn Garden City, all of England

[73] Assignee: Smith Kline & French Laboratories Limited, Welwyn Garden City, England

[21] Appl. No.: 549,953

[22] Filed: Nov. 9, 1983

Related U.S. Application Data

[62] Division of Ser. No. 290,628, Aug. 6, 1981, which is a division of Ser. No. 56,171, Jul. 10, 1979, Pat. No. 4,305,945.

[30]  Foreign Application Priority Data

Jul. 15, 1978 [GB] United Kingdom ............... 7829999

[51] Int. Cl.$^4$ ................ C07D 239/02; C07D 403/00
[52] U.S. Cl. ................................ 544/320; 544/238; 544/296
[58] Field of Search ................ 544/320, 296, 238

[56] References Cited

U.S. PATENT DOCUMENTS

| | | | |
|---|---|---|---|
| 4,145,546 | 3/1979 | Brown et al. | 544/310 |
| 4,218,452 | 8/1980 | Brown et al. | 544/321 |
| 4,305,945 | 12/1981 | Ganellin et al. | 544/320 |
| 4,439,435 | 3/1984 | Ganellin et al. | 544/320 |

OTHER PUBLICATIONS

Agai et al., Chem. Abst., vol. 81 (1974), 120567j.
Reiter et al., Chem. Abst., vol. 84 (1976), 4172q.

Primary Examiner—Donald G. Daus
Assistant Examiner—Cecilia Shen
Attorney, Agent, or Firm—Joan S. Keps; Richard D. Foggio; Alan D. Lourie

[57]  ABSTRACT

The compounds are isoureas and isothioureas which have an O- or S- alkylpyrimidone substituent and which are histamine $H_2$-antagonists and antiinflammatory agents. A specific compound of this invention is 2-[5-(O-isoureido)pentylamino]-5-(6-methyl-3-pyridylmethyl)-4-pyrimidone.

2 Claims, No Drawings

2-SUBSTITUTED ALKYLAMINOPYRIMIDONES

This is a division of application Ser. No. 290,628 filed Aug. 6, 1981, which is a division of Ser. No. 056,171 filed July 10, 1979 now U.S. Pat. No. 4,305,945.

This invention relates to pyrimidine compounds, to pharmaceutical compositions containing them and to methods of blocking histamine $H_2$-receptors by administering them.

Many physiologically-active substances elicit their biological actions by interaction with specific sites known as receptors. Histamine is such a substance and has multiple biological actions. Those biological actions of histamine which are inhibited by drugs commonly called "antihistamines" (histamine $H_1$-antagonists), of which mepyramine, diphenydramine and chlorpheniramine are typical examples, are mediated through histamine $H_1$-receptors. However, others of the biological actions of histamine are not inhibited by "antihistamines" (histamine $H_1$-antagonists) and actions of this type which are inhibited by burimamide are mediated through receptors which are termed histamine $H_2$-receptors. In this specification by histamine $H_2$-receptors is meant receptors defined by Black et al. (Nature, 236, 385 (1972)) as those histamine receptors which are not blocked by mepyramine but are blocked by burimamide. Compounds which block histamine $H_2$-receptors are referred to as histamine $H_2$-antagonists.

Blockade of histamine $H_2$-receptors is of value in inhibiting the biological actions of histamine which are not inhibited by "antihistamines" (histamine $H_1$-antagonists). Histamine $H_2$-antagonists are active, for example, as inhibitors of gastric acid secretion, as anti-inflammatory agents and as agents which act on the cardiovascular system, for example as inhibitors of the effects of histamine on blood pressure.

In some physiological conditions the biological actions of histamine are mediated through both histamine $H_1$- and $H_2$-receptors and blockade of both types of receptors is useful. These conditions include inflammation mediated by histamine, for example skin inflammation, and those hypersensitivity responses due to the action of histamine at $H_1$- and $H_2$-receptors, for example allergies.

The pyrimidine compounds of the present invention are histamine $H_2$-antagonists and also have histamine $H_1$-antagonist activity and antiinflammatory activity.

The present invention provides pyrimidines of Structure 1:

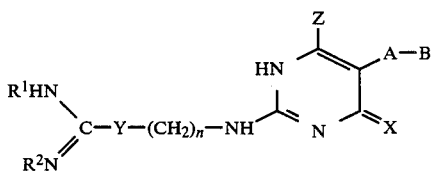

in which $R^1$ and $R^2$ (which may be the same or different) are hydrogen or lower alkyl or together with the carbon and two nitrogen atoms shown form a dihydroimidazolyl or tetrahydropyrimidyl group;
Y is sulphur or oxygen;
n is from 3 to 8;
X is oxygen or sulphur;
Z is hydrogen or lower alkyl;
A is straight or branched $C_1$–$C_5$ alkylene or —$(CH_2)_pW(CH_2)_q$— where W is oxygen or sulphur and the sum of p and q is 1 to 4;
and B is methyl, $C_3$–$C_6$ cycloalkyl, a heteroaryl group optionally substituted by one or more (which may be the same or different) lower alkyl, lower alkoxy, halo, hydroxy or amino groups, or B is a naphthyl, 5- or 6-(2,3-dihydro-1,4-benzodioxinyl), or a 4- or 5-(1,3-benzodioxolyl) group, or a phenyl group optionally substituted with one or more (which may be the same or different) lower alkyl, lower alkoxy, halogen, aryl(lower alkoxy) (preferably phenyl(lower alkoxy), for example benzyloxy), hydroxy, lower alkoxy-lower alkoxy, trifluoromethyl, di(lower alkyl)amino, phenoxy, halophenoxy, lower alkoxyphenoxy, phenyl, halophenyl or lower alkoxyphenyl groups, or, provided A is alkylene, B can be hydrogen.

The compounds of Structure 1 can be in the form of the free bases or their pharmaceutically acceptable acid addition salts.

Throughout this specification by the terms 'lower alkyl' and 'lower alkoxy' are meant alkyl and alkoxy groups which can be straight or branched and which contain 1 to 4 carbon atoms. Particular lower alkyl groups are methyl, ethyl, 1-propyl and 2-propyl. Particular lower alkoxy groups are methoxy, ethoxy, 1-propoxy and 2-propoxy.

Examples of heteroaryl groups B are pyridyl, N-oxopyridyl, furyl, thienyl, thiazolyl, oxazolyl, isothiazolyl, imidazolyl, pyrimidyl, pyrazyl, pyridazyl, thiadiazolyl, quinolyl, isoquinolyl, 5,6,7,8-tetrahydroquinolyl, 1,3-dioxolopyridyl, benzimidazolyl and benzthiazolyl.

Particular heteroaryl groups are 2-furyl, 2-thienyl, 2-pyridyl, 3-pyridyl, 4-pyridyl, 2-thiazolyl, 2-imidazolyl, 2-pyrimidyl, 2-pyrazyl, 3-pyridazyl, 3-quinolyl and 1-isoquinolyl optionally substituted by one or more lower alkyl or lower alkoxy groups. Specific heteroaryl groups are 2-furyl, 3-pyridyl, 6-methyl-3-pyridyl, 5,6-dimethyl-3-pyridyl, 6-methoxy-3-pyridyl, 2-methoxy-4-pyridyl, 4-methoxy-2-pyridyl, 4-hydroxy-2-pyridyl, 6-hydroxy-3-pyridyl, 2-hydroxy-4-pyridyl, N-oxo-3-pyridyl and N-oxo-6-methyl-3-pyridyl.

Preferably X is oxygen.
Preferably Z is hydrogen.
Preferably $R^1$ and $R^2$ are both hydrogen.
Preferably Y is oxygen.
Preferably n is 3 to 6, particularly 5 or 6.

When B is an optionally substituted phenyl group it is preferably substituted by one or more lower alkoxy groups, and in particular is 3-methoxyphenyl or 3,4-dimethoxyphenyl.

A particularly valuable group of compounds are those in which B is a 6-(2,3-dihydro-1,4-benzodioxinyl) or 5-(1,3-benzodioxolyl) group.

Preferably in the compounds of Structure 1 either A is an alkylene group, for example 1,1-ethanediyl (=CHCH$_3$), 1,2-ethanediyl (—CH$_2$CH$_2$—), 1,3-propanediyl (—CH$_2$CH$_2$CH$_2$—) and especially methylene (—CH$_2$—), or A is oxymethyl (—OCH$_2$—) where p is 0, W is oxygen and q is 1.

Examples of specific compounds are:
2-[5-(S-isothioureido)-pentylamino]-5-(3-pyridylmethyl)-4-pyrimidone,
2-[6-(S-isothioureido)hexylamino]-5-(3-pyridylmethyl)-4-pyrimidone,
2-[5-(O-isoureido)pentylamino]-5-(3-pyridylmethyl)-4-pyrimidone, and 2-[5-(O-isoureido)pentylamino]-5-(6-methyl-3-pyridyl-methyl)-4-pyrimidone.

The compounds of Structure 1 are shown and described as 4-pyrimidone and 4-thione derivatives and these derivatives exist in equilibrium with the corresponding 6-one and 6-thione tautomers. These compounds also exist to a lesser extent as the mercapto and hydroxy tautomers, and the pyrimidine ring may also exist in the following tautomeric forms:

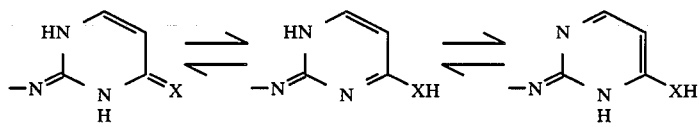

The isothioureido and isoureido groups can also exist in tautomeric forms, and it will be understood that all these tautomeric forms are within the scope of the present invention. Hydrates and hydrated acid addition salts of compounds of Structure 1 are also within the scope of this invention.

This invention includes the obvious chemical equivalents of the compounds of Structure 1, for example, those compounds in which the —$(CH_2)_n$— group has additional substitiuents which do not substantially qualitatively affect the essential utility possessed by the compounds of Structure 1.

The compounds of Structure 1 can be prepared by reacting a compound of Structure 2

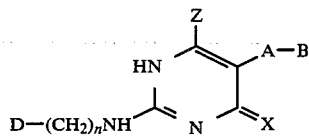

where D is HY- or a leaving group, with (a) when D is HY-, an isothiourea of Structure 3, in which E is lower alkyl or aryl(lower alkyl) (for example benzyl), or a cyanamide $R^1HNCN$ or carbodiimide $R^1N=C=NR^2$, or (b) when D is a leaving group, a urea or thiourea of Structure 4

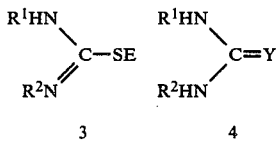

Typical leaving groups are chlorine, bromine, iodine, arylsulphonyloxy (for example toluene-p-sulphonyloxy) and methanesulphonyloxy.

When a compound of Structure 2 in which D is HY- is reacted with an isothiourea of Structure 3 preferably E in the isothiourea of Structure 3 is methyl. Preferably the reaction is carried out in the presence of a non-nucleophilic base. Preferably when Y is oxygen a strong base is used, for example sodium hydride or potassium t-butoxide, in a dipolar aprotic solvent, for example dimethylformamide, and preferably the reaction is carried out at an elevated temperature, for example 70° to 100° C. Preferably when Y is sulphur a base of moderate strength is used for example potassium carbonate or triethylamine, and the reaction is carried out at about room temperature in a lower alkanol or an aqueous mixture of a lower alkanol.

When a compound of Structure 2 in which D is HY- (HO- or HS-) is reacted with a cyanamide $R^1HNCN$ or carbodiimide $R^1N=C=NR^2$ preferably the reaction is carried out in the presence of a copper catalyst or under anhydrous acidic conditions, for example using a salt of the compound of Structure 2 with one equivalent of hydrogen chloride in an inert diluent, for example benzene or toluene.

When a compound of Structure 2 in which D is a leaving group is reacted with a urea or thiourea of Structure 4, preferably the reaction is carried out under neutral conditions, that is using a neutral acid addition salt of the pyrimidone of Structure 2, particularly a hydrochloride or hydrobromide and preferably under essentially anhydrous conditions. Preferably the reaction is carried out in a polar solvent, for example a lower alkanol, at an elevated temperature, for example 50° to 150° C. Preferably, when Y is Structure 4 is sulphur, D in the compound of Structure 2 is chlorine, bromine or iodine, especially chlorine or bromine, and when Y is oxygen preferably D is iodine or toluene-p-sulphonyloxy.

The compounds of Structure 1 in which Y is oxygen can also be prepared by reacting a compound of Structure 6, in which G is lower alkylthio, chlorine, bromine or $NO_2NH$—, with an isourea of Structure 5.

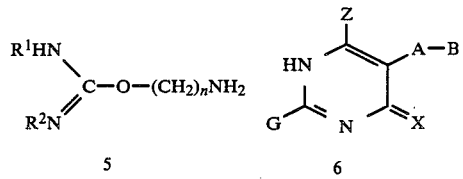

Preferably this reaction is carried out in an inert solvent, for example pyridine, at an elevated temperature, for example the reflux temperature. Preferably G is $NO_2NH$— and preferably this reaction is carried out in pyridine or in a lower alkanol, for example ethanol or 2-propanol, when the reaction is preferably carried out at the boiling point of the lower alkanol.

All the reactions described above involve two reactants and preferably approximately equimolecular amounts of the reactants are used, although an excess, for example a slight excess of from 1.1 to 1.5 molar equivalents or a larger excess of from 1.5 to 4 molar equivalents, of either reactant can be used. An excess of either reactant can be present at the start of the reaction or can be added during the course of the reaction.

The intermediates of Structure 5 can be prepared by reacting an isothiourea of Structure 3 with an aminoalcohol of formula $HO(CH_2)_nNH_2$ and a strong base. Preferably this reaction is carried out using sodium hydride as the strong base. Preferably this reaction is carried out using dioxan or tetrahydrofuran as solvent.

The intermediates of Structure 5 in which $R^1$ and $R^2$ are hydrogen or lower alkyl can be prepared by treating cyanamide, an alkylcyanamide or a N,N'-dialkylcarbodiimide with a hydrohalide salt of an aminoalcohol or formula HO(CH$_2$)$_n$NH$_2$ under anhydrous acidic conditions, or in the presence of a copper catalyst.

The intermediates of Structure 2 in which X is oxygen and D is a leaving group can be prepared from the corresponding alcohols of Structure 2 in which D is HO-, e.g. by treatment with thionyl chloride or bromide, toluene-p-sulphonyl chloride or methanesulphonyl chloride or treatment of the chloro compound sodium iodide. The alcohols of Structure 2 in which D is HO- and X is oxygen can be prepared by reacting a compound of Structure 6 with an α,ω-aminoalkanol HO(CH$_2$)$_n$NH$_2$.

The compounds of Structure 6 in which X is oxygen and G is nitroamino can be prepared by reacting a β-oxoester of Structure 7,

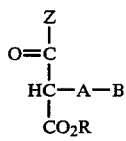
                                       7 in which R is lower alkyl, with nitroguanidine. Preferably this reaction is carried out in the presence of a base, for example an alkali metal hydroxide or lower alkoxide or sodium hydride.

The pyrimid-4-thiones of Structure 6 in which X is sulphur and G is lower alkylthio, chlorine or bromine, can be prepared by the alkaline hydrolysis, for example with sodium hydroxide in aqueous methanol, of the corresponding S-pyrimidyl di(lower alkyl)thiocarbamate. The S-pyrimidyl di(lower alkyl)thiocarbamates can be prepared by reacting a pyrimidone of Structure 6 in which X is oxygen with a di(lower alkyl)thiocarbamyl chloride and a base, for example sodium hydride, and heating the product, for example at 180° for 30 minutes, until it has rearranged from an O- to a S-pyrimidyl thiocarbamate.

Compounds of Structure 6 in which G is chlorine, bromine or NO$_2$NH— and B is N-oxopyridyl can be prepared by reacting the corresponding compound of Structure 6 in which B is pyridyl with a peroxycarboxylic acid, for example 3-chloroperoxybenzoic acid, peroxybenzoic acid or peracetic acid.

The compounds of Structure 1 block histamine H$_2$-receptors; for example, they inhibit histamine-stimulated secretion of gastric acid from the lumen-perfused stomachs of rats anaesthetised with urethane, at doses of from 0.1 to 256 micromoles per kilogram intravenously. This procedure is referred to in Ash and Schild, Brit. J. Pharmac. Chemother. 27, 427 (1966). The 5 specific compounds described as the products of Examples 1 to 5 were found to produce 50% inhibition at intravenous doses of less than 1 micromole per kilogram. Their activity as histamine H$_2$-antagonists is also demonstrated by their ability to inhibit other actions of histamine which, according to the above mentioned paper of Ash and Schild, are not mediated by histamine H$_1$-receptors. For example, they inhibit the actions of histamine on the isolated guinea pig atrium and isolated rat uterus. They inhibit the basal secretion of gastric acid and also that stimulated by pentagastrin or by food. In a conventional test such as the measurement of blood pressure in the anaesthetised cat, at doses of from 0.5 to 256 micromoles per kilogram intravenously, they inhibit the vasodilator action of histamine. The potency of these compounds is illustrated by the effective dose producing 50% inhibition of gastric acid secretion in the anaesthetised rat and the dose producing 50% inhibition of histamine-induced tachycardia in the isolated guinea pig atrium (less than 10$^{-4}$ Molar).

The compounds of Structure 1 also block histamine H$_1$-receptors, that is they inhibit the biological actions of histamine which are inhibited by mepyramine, diphenhydramine and chlorpheniramine. For example they inhibit the histamine-stimulated contractions of the isolated guinea-pig ileum at doses of about 10$^{-5}$ Molar. Their combined histamine H$_1$- and H$_2$-antagonist activity is useful for treatment of inflammation in conditions where histamine is a mediator of inflammation, for instance in skin inflammation. Their combined histamine H$_1$- and H$_2$- activity is also useful in those circumstances where there are hypersensitivity responses, for example, allergies, due to the action of histamine at H$_1$- and H$_2$-receptors. It is advantageous to administer a single compound having histamine H$_1$- and H$_2$-antagonist activity rather than to administer individual compounds having histamine H$_1$-antagonist activity and histamine H$_2$-antagonist activity as difficulties arising from differing rates of absorption and pharmacokinetic characteristics are avoided.

The compounds of Structure 1 show antiinflammatory activity in conventional tests such as the rat or mouse paw oedema and the guinea-pig U.V. erythema tests. In the former tests the oedema is induced by an irritant, for example carrageenan, and in the latter test the depilated skin of the guinea-pig is exposed to U.V. radiation and an erythema results. Subcutaneous injection of doses of the compound of Structure 1 reduces the rat or mouse paw volume in the former tests and reduces the intensity of the guinea-pig erythema in the latter test. A useful modification of the guinea-pig U.V. erythema test is to irradiate only the whole ear and measure the ear temperature by a thermistor probe. Subcutaneous injection of doses of about 0.2 mmol/kg of a compound of Structure 1 to a guinea-pig reduces the rise in ear temperature caused by U.V. irradiation. These compounds show a sustained anti-inflammatory activity in this test greater than that which may reasonable be attributed to blockade of histamine receptors. Activity in this animal test is indicative that the compounds will be useful in treating inflammatory conditions in humans.

The pharmaceutical compositions of the invention comprise a pharmaceutical carrier and a pharmacologically-active compound of Structure 1 which can be in the base form or in the form of a pharmaceutically acceptable acid addition salt. Such addition salts include those with hydrochloric, hydrobromic, hydriodic, sulphuric and maleic acids and may conveniently be formed from the corresponding compounds of Structure 1 by standard procedures, for example by treating them with an acid in a lower alkanol or by the use of ion-exchange resins to form the required salt either directly from the compound in the base form from a different addition salt. Preferably the compounds of Structure 1 in which Y is sulphur are used in the form of acid addition salts and compounds in which Y is oxygen are used in the form of the free bases.

The pharmaceutical carrier employed can be a solid or liquid. Examples of solid carriers are lactose, maize starch, potato starch, or modified starches, dicalcium phosphate, terra alba, sucrose, celluloses, talc, gelatin, agar, pectin, acacia, magnesium stearate and stearic acid. Examples of liquid carriers are syrup, peanut oil, olive oil, alcohol, propylene glycol, polyethylene glycols and water.

If a solid carrier is used, the composition can be prepared in the form of a tablet, capsule containing power or pellets, troche or lozenge. The amount of solid carrier in a unit dosage form is generally from about 25 mg to about 300 mg. If a liquid carrier is used, the composition can be in the form of a syrup, emulsion, multiple emulsion, sterile injectable liquid or an aqueous or non-aqueous solution or liquid suspension. Other additives such as preservatives, for example antioxidants or antibacterials, and/or flavouring of colouring agents can also be included. The sterile liquids can be prepared in ampoules, multidose vials or unit dose disposable systems. The preparation can also be in a semi-solid form, for example a cream, paste, ointment or gel, or in a liquid or aerosol form for topical application. The pharmaceutical compositions are prepared by conventional techniques involving procedures such as milling, mixing, granulating and compressing, spray drying, freeze drying or dissolving or dispersing the ingredients as appropriate to the desired preparation. The active ingredient will be present in the compositions in an effective amount to produce the desired activity. Preferably, each dosage unit will contain the active ingredient in an amount of from about 50 mg to about 250 mg.

The invention provides a method of producing antiinflammatory activity which comprises administering to an animal an active compound of Structure 1. The active ingredient will preferably be administered one to six times per day. The invention also provides a method of blocking histamine $H_2$-receptors and a method of simultaneously blocking histamine $H_1$- and $H_2$-receptors which comprises administering to an animal an active compound of Structure 1. The active compound will be administered in an effective amount to product said activity. The daily dosage regimen will preferably be from about 150 mg to about 1500 mg. The route of administration may be oral, parenteral or, when appropriate, topical.

The invention is illustrated by the following Examples, in which temperatures are in °C:

EXAMPLE 1

(i) 2-Methylthio-5-(3-pyridylmethyl)-4-pyrimidone (23.3 g) and 5-aminopentanol (24.5 g) were fused together at 170°-180° for 2 hours. Water was added to the cooled residue and the mixture was adjusted to pH7 with dilute hydrochloric acid. The solid (23.8 g) which crystallised out was recrystallised from 2-propanol containing hydrogen chloride to give 2-(5-hydroxypentylamino)-5-(3-pyridylmethyl)-4-pyrimidone dihydrochloride, m.p. 203°-205°.

(ii) 2-(5-Hydroxypentylamino)-5-(3-pyridylmethyl)-4-pyrimidone dihydrochloride (1.9 g) was heated under reflux in thionyl chloride (25 ml) for 45 minutes. The mixture was evaporated to dryness to give crude 2-(5-chloropentylamino)-5-(3-pyridylmethyl)-4-pyrimidone dihydrochloride, which was treated with thiourea (0.47 g) dissolved in the minimum volume of hot ethanol. The ethanol was boiled off and the residue was heated at 160° for 4 hours. The residue was extracted with boiling ethanol and the extract cooled. The solid (1.85 g) which crystallised out was dissolved in water, the solution was adjusted to pH7–7.5 with aqueous sodium hydroxide and this solution was extracted with chloroform. The aqueous phase was evaporated to a residue which was extracted with 2-propanol and the extract was evaporated to give 2-[5-(S-isothioureido)pentylamino]-5-(3-pyridylmethyl)-4-pyrimidone monohydrochloride as an oil which was treated with hydrogen chloride in ethanol and crystallised from methanol-ethanol to give 2-[5-(S-isothioureido)pentylamino]-5-(3-pyridylmethyl)-4-pyrimidone trihydrochloride (1.5 g) m.p. 228°-9°.

EXAMPLE 2

(i) Substitution of 6-aminohexanol for 5-aminopentanol in the procedure of Example 1(i) gave 2-(6-hydroxyhexylamino)-5-(3-pyridylmethyl)-4-pyrimidone, m.p. 131°-133°.

(ii) Substitution of 2-(6-hydroxyhexylamino)-5-(3-pyridylmethyl)-4-pyrimidone for 2-(5-hydroxypentylamino)-5-(3-pyridylmethyl)-4-pyrimidone in the procedure of Example 1(ii) gave 2-[6-(isothioureido)hexylamino[-5-(3-pyridylmethyl)-4-pyrimidone trihydrochloride, which was dissolved in water and passed down an Amberlite IRA 400 ion-exchange resin (acetate form). Amberlite IRA 400 is a quaternary ammonium ion-exchange resin with a matrix of 8% crosslinked polystyrene-divinylbenzene. The solution was evaporated to dryness and the residue was recrystallised from methanol-ether to give 2-[6-(S-isothioureido)hexylamino]-5-(3-pyridylmethyl)-4-pyrimidone, acetic acid salt, m.p. 160°-163°.

EXAMPLE 3

Dry hydrogen chloride (1.7 g) was added to a suspension of 2-(5-hydroxypentylamino)-5-(3-pyridylmethyl)-4-pyrimidone dihydrochloride (13.0 g) and cyanamide (3.0 g) in dry benzene (100 ml) and the mixture was allowed to stand at room temperature for 5 days. Cyanamide (1.5 g) was added, the mixture was thoroughly stirred and was left to stand at room temperature for a further 7 days. The benzene was decanted off and the solid was dissolved in water (150 ml). The solution was adjusted to pH7.5 and extracted with n-butanol (4×250 ml) and aqueous extracts (6×100 ml) were made of the butanol extracts using a countercurrent distribution technique. The aqueous extracts were concentrated, acidified with hydrochloric acid and passed down in Amberlite IRA 400 (Bromide form) ion-exchange column. The eluent was evaporated to dryness and the residue was crystallised from ethanol/2-propanol to give 2-[5-(O-isoureido)pentylamino]-5-(3-pyridylmethyl)-4-pyrimidone trihydrobromide, m.p. 158°-160° (decomp). This is converted into the free base by passage down a quaternary ammonium ion-exchange resin in the OH$^-$ form.

EXAMPLE 4

Substitution of an equivalent amount of N, N'-dimethylthiourea for thiourea in the procedure of Example 1(ii) gave 2-[5-(N,N'-dimethyl-S-isothioureido)pentylamino]-5-(3-pyridylmethyl)-4-pyrimidone trihydrochloride monohydrate, as a glass, m.p. indeterminate.

| 100 MHz $^1$H n.m.r. (D$_2$O): δ | | | | |
|---|---|---|---|---|
| ~1.70 | —(CH$_2$)$_3$— | m | (6.0) | |
| 3.06, 3.11 | NCH$_3$ | 2s | | ⎫ |
| | | | | ⎬ (8.4) |
| ~3.21 | SCH$_2$ | m | | ⎭ |
| ~3.50 | —CH$_2$N | m | (2.0) | |

| | | | |
|---|---|---|---|
| 4.01 | \>—CH₂—/ | s | (2.0 ref) |
| 7.84 | H—C(=O)—H | s | (1.0) |
| 8.09 | Pyr 5-H | d of d | (1.0) |
| 8.61 | Pyr 4-H | m | ⎫ (3.0) |
| ~8.75 | Pyr 2-H + 6-H | m | ⎭ |

EXAMPLE 5

(i) 3-(6-Methyl-3-pyridyl)propenoic acid, m.p. 213.5°–215.5°, was prepared by reacting 6-methylpyridine-3-carboxaldehyde with malonic acid in pyridine with piperidine catalyst, and was converted into the corresponding ethyl ester m.p. 36°–37° which was reduced with hydrogen and palladium-on-charcoal catalyst to give ethyl 3-(6-methyl-3-pyridyl)-propionate (oil). This ester was reacted with sodium and ethyl formate and the product treated with thiourea to give 5-(6-methyl-3-pyridylmethyl)-2-thiouracil m.p. 240°–241° which was alkylated with methyl iodide in the presence of sodium hydroxide at 70° to give 5-(6-methyl-3-pyridylmethyl)-2-methylthio-4-pyrimidone, m.p. 197°–198.5°.

(ii) Reaction of 5-(6-methyl-3-pyridylmethyl)-2-methylthio-4-pyrimidone with 5-aminopentanol at 170°–180° gave 2-(5-hydroxypentylamino)-5-(6-methyl-3-pyridylmethyl)-4-pyrimidone which was isolated as the dihydrochloride salt m.p. 215°–217°.

(iii) Substitution of 2-(5-hydroxypentylamino)-5-(6-methyl-3-pyridylmethyl)-4-pyrimidone for 2-(5-hydroxypentylamino)-5-(3-pyridylmethyl)-4-pyrimidone in the general procedure of Example 3 gave 2-[5-(O-isoureido)pentylamino]-5-(6-methyl-3-pyridylmethyl)-4-pyrimidone trihydrobromide monohydrate m.p. 110°–115° (from ethanol/2-propanol).

| ¹H n.m.r (100 MHz, D₂O): −δ | | | |
|---|---|---|---|
| 1.70 | —CH₂— | m | (6.1) |
| 2.77 | —CH₃ | s | (3.0 ref) |
| 3.46 | N—CH₂— | m | (2.1) |
| 3.90 | \>—CH₂—/ | s | (1.8) |
| 4.30 | —OCH₂— | m | (obscured by D₂O) |
| 7.74 | Pyrim 6-H | s | ⎫ (2.0) |
| 7.84 | Pyr 5-H | d | ⎭ |
| 8.39 | Pyr 4-H | m | ⎫ (2.0) |
| 8.56 | Pyr 2-H | m | ⎭ |

This is converted into the free base by passage down a quaternary ammonium ion-exchange resin in the OH⁻ form.

EXAMPLE 6

Treatment of 5-(6-methyl-3-pyridylmethyl)-2-methylthio-4-pyrimidone with 6-aminohexanol gives 2-(6-hydroxyhexylamino)-5-(6-methyl-3-pyridylmethyl)-4-pyrimidone which may be successively treated with thionyl chloride and thiourea according to the general procedure of Example 1(ii) to give 2-[6-(S-isothioureido)hexlamino]-5-(6-methyl-3-pyridylmethyl)-4-pyrimidone trihydrochloride.

EXAMPLE 7

Substitution of 2-(6-hydroxyhexylamino)-5-(6-methyl-3-pyridylmethyl)-4-pyrimidone for 2-(5-hydroxypentylamino)-5-(3-pyridylmethyl)-4-pyrimidone in the general procedure of Example 3 gives 2-[6-((O-isoureido)-hexylamino]-5-(6-methyl-3-pyridylmethyl)-4-pyrimidone.

EXAMPLE 8

When 2-(5-hydroxypentylamino)-5-(6-methyl-3-pyridylmethyl)-4-pyrimidone is successively reacted with thionyl chloride and thiourea according to the general procedure of Example 1(ii) the product is 2-[5-(S-isothioureido)pentylamino]-5-(6-methyl-3-pyridylmethyl)-4-pyrimidone trihydrochloride.

EXAMPLES 9 AND 10

(i) Reaction of 5-[5-(1,3-benzodioxolyl)methyl]-2-methylthio-4-pyrimidone with
(a) 5-aminopentanol
(b) 6-aminohexanol
(a) 2-[5-(S-isothioureido)pentylamino]-5-[5-(1,3-benzodioxolyl)methyl]-4-pyrimidone
(b) 2-[6-(S-isothioureido)hexylamino]-5-[5-(1,3-benzodioxolyl)methyl]-4-pyrimidone
(ii) Substitution of
(a) 2-(5-hydroxypentylamino)-5-[5-(1,3-benzodioxolyl)methyl]-4-pyrimidone
(b) 2-(6-hydroxyhexylamino)-5-[5-(1,3-benzodioxolyl)methyl]-4-pyrimidone
for 2-(5-hydroxypentylaminio)-5-(3-pyridylmethyl)-4-pyrimidone in the general procedure of Example 3 gives
9(a) 2-[5-(O-isoureido)pentylamino]-5-[5-(1,3-benzodioxolyl)methyl]-4-pyrimidone
10(b) 2-[6-(O-isoureido)hexylamino]-5-[5-(1,3-benzodioxolyl)methyl]-4-pyrimidone

EXAMPLE 11

(i) Ethyl 3-(6-methyl-3-pyridyl)propionate was reacted at 0° with ethyl formate and sodium hydride in 1,2-dimethoxyethane to give ethyl 2-formyl-3-(6-methyl-3-pyridyl)propionate, m.p. 142°–144°, which was heated under reflux with dried nitroguanidine and sodium methoxide in methanol to give 2-nitroamino-5-(6-methyl-3-pyridylmethyl)-4-pyrimidone, m.p. 215°–6° (decomp).

(ii) Reaction of 2-nitroamino-5-(6-methyl-3-pyridylmethyl)-4-pyrimidone with 5-aminopentanol in refluxing pyridine gives 2-(5-hydroxypentylamino)-5-(6-methyl-3-pyridylmethyl)-4-pyrimidone which can be converted into 2-[5-(O-isoureido)pentylamino]-5-(6-methyl-3-pyridylmethyl)-4-pyrimidone by the procedure of Example 5(iii).

EXAMPLE 12

S-Methylisothiourea is reacted with 5-aminopentanol and sodium hydride in tetrahydrofuran to give O-(5-aminopentyl)isourea, which is reacted with 2-nitroamino-5-(6-methyl-3-pyridylmethyl)-4-pyrimidone in refluxing ethanol to give 2-[5-(O-isoureido)pentylamino]-5-(6-methyl-3-pyridylmethyl)-4-pyrimidone.

EXAMPLES 13 TO 16

2-(5-Hydroxypentylamino)-5-(6-methyl-3-pyridylmethyl)-4-pyrimidone is reacted with (a) 1,4,5,6-tetrahydro-2-methylthiopyrimidine
(b) 4,5-dihydro-2-methylthiomidazole
(c) N,S-dimethylisothiourea
(d) N,N'-dibutyl-S-methylisothiourea and sodium hydride in dimethylformamide to give

EXAMPLE 13

2-[5-(1,4,5,6-tetrahydro-2-pyrimidyloxy)pentylamino]-5-(6-methyl-3-pyridylmethyl)-4-pyrimidone

EXAMPLE 14

2-[5-(4,5-dihydro-2-imidazolyloxy)pentylamino]-5-(6-methyl-3-pyridylmethyl)-4-pyrimidone

EXAMPLE 15

2-[5-(N-methyl-S-isothioureido)pentylamino]-5-(6-methyl-3-pyridylmethyl)-4-pyrimidone

EXAMPLE 16

2-[5-(N,N'-dibutyl-S-isothioureido)pentylamino]-5-(6-methyl-3-pyridylmethyl)-4-pyrimidone

EXAMPLE 17 TO 19

Reaction of 2-methylthio-5-(6-methyl-3-pyridylmethyl)-4-pyrimidone with
(a) 3aminopropanol
(b) 7-aminoheptanol
(c) 8-aminooctanol
at 160° gives
(a) 2-(3-hydroxypropylamino)-5-(6-methyl-3-pyridylmethyl)-4-pyrimidone
(b) 2-(7-hydroxyheptylamino)-5-(6-methyl-3-pyridylmethyl)-4-pyrimidone
(c) 2-(8-hydroxyoctylamino)-5-(6-methyl-3-pyridylmethyl)-4-pyrimidone
which are reacted with cyanamide and hydrogen chloride to give

EXAMPLE 17

2-[3-(O-isoureido)propylamino]-5-(6-methyl-3-pyridylmethyl)-4-pyrimidone

EXAMPLE 18

2-[7-(O-isoureido)heptylamino]-5-(6-methyl-3-pyridylmethyl)-4-pyrimidone

EXAMPLE 19

2-[8-(O-isoureido)octylamino]-5-(6-methyl-3-pyridylmethyl)-4-pyrimidone

EXAMPLES 20 AND 21

Reaction of 5-aminopentanol at 160° with
(a) 6-methyl-2-methylthio-5-(3-pyridylmethyl)-4-pyrimidone
(b) 2-methylthio-5-(1-(3-pyridyl)ethyl)-4-pyrimidone
gives
(a) 2-(5-hydroxypentylamino)-6-methyl-5-(3-pyridylmethyl)-4-pyrimidone
(b) 2-(5-hydroxypentylamino)-5-(1-(3-pyridyl)ethyl)-4-pyrimidone
which are reacted with cyanamide and hydrogen chloride to give

EXAMPLE 20

2-[5-(O-isoureido)pentylamino]-6-methyl-5-(3-pyridylmethyl)-4-pyrimidone

EXAMPLE 21

2-[5-(O-isoureido)pentylamino)-5-(1-(3-pyridyl)ethyl)-4-pyrimidone

EXAMPLE 22

5-(6-Methyl-3-pyridylmethyl)-2-methylthio-4-pyrimidone is reacted with dimethylthiocarbamyl chloride and sodium hydride to give O-[5-(6-methyl-3-pyridylmethyl)-2-methylthio-4-pyrimidyl]dimethylthiocarbamate. This is heated at 180° for 30 minutes to give S-[5-(6-methyl-3-pyridylmethyl)-2-methylthio-4-pyrimidyl]dimethylthiocarbamate which is treated with sodium hydroxide in methanol to give 5-(6-methyl-3-pyridylmethyl)-2-methylthiopyrimide-4-thione, which is heated with 5-aminopentanol at 150° to give 2-(5-hydroxypentylamino)-5-(6-methyl-3-pyridylmethyl)-pyrimide-4-thione. This is reacted with cyanamide and hydrogen chloride to give 2-[5-(O-isoureido)pentylamino]-5-(6-methyl-3-pyridylmethyl)-pyrimid-4-thione.

EXAMPLE 23

(i) Ethyl formate and 2-butanone are added to sodium hydride and cyanoacetamide is added to give 3-cyano-5,6-dimethyl-2-hydroxypyridine, which is reacted with phosphorus pentachloride and the product reduced with hydrogen and Raney nickel in the presence of semicarbazide, and formaldehyde is added to the mixture to give 2-chloro-5,6-dimethyl-3-pyridinecarboxaldehyde m.p. 69°-70°.

(ii) 2-Chloro-5,6-dimethyl-3-pyridinecarboxaldehyde is condensed with malonic acid and the product is esterified and reduced with hydrogen at 344 kPa using palladium-on-charcoal catalyst to give ethyl 3-(5,6-dimethyl-3-pyridyl)propionate as an oil. This oil is reacted with ethyl formate and sodium hydride at room temperature to give the 2-formyl derivative, m.p. 148°-9°, which is heated under reflux with nitroguanidine and sodium methoxide to give 5-(5,6-dimethyl-3-pyridylmethyl)-2-nitroamino-4-pyrimidone, m.p. 212°-3°.

(iii) 5-(5,6-Dimethyl-3-pyridylmethyl)-2-nitroamino-4-pyrimidone is reacted with 5-aminopentanol in refluxing ethanol to give 2-(5-hydroxypentylamino)-5-(5,6-dimethyl-3-pyridylmethyl)-4-pyrimidone which is reacted with cyanamide and hydrogen chloride to give 2-[5-(O-isoureido)pentylamino]-5-(5,6-dimethyl-3-pyridylmethyl)-4-pyrimidone.

EXAMPLES 24 TO 29

(i) Reduction of 2-methoxy-5-cyanopyridine with hydrogen and Raney nickel in the presence of semicarbazide, and treatment of the mixture with formaldehyde gives 6-methoxypyridine-3-carboxaldehyde, m.p. 48°-9°. In a similar manner 2-methoxypyridine-4-carboxaldehyde, m.p. 33°-6° is prepared from 2-methoxy-4-cyanopyridine (which is prepared from 2-chloro-4-cyanopyridine and sodium methoxide).

(ii) Condensation of
(a) 6-methoxypyridine-3-carboxaldehyde
(b) 2-methoxypyridine-4-carboxaldehyde
(c) 4-methoxypyridine-2-carboxaldehyde
with malonic acid and esterification and reduction of the product with hydrogen and palladium-on-charcoal gives the corresponding 3-(pyridyl)propionates which are formylated with ethyl formate and sodium hydride and the product reacted with nitroguanidine and sodium methoxide to give (a) 2-nitroamino-5-(6-methoxy-3-pyridylmethyl)-4-pyrimidone m.p. 183.5°–186°.
(b) 2-nitroamino-5-(2-methoxy-4-pyridylmethyl)-4-pyrimidone m.p. 194°–195.5°.
(c) 2-nitroamino-5-(4-methoxy-2-pyridylmethyl)-4-pyrimidone m.p. 196°–8°.

(iii) Reaction of the above 2-nitroamino-4-pyrimidones with 5-aminopentanol gives the corresponding 2-(5-hydroxypentylamino)-4-pyrimidones which are reacted with S-methylisothiourea and sodium hydride to give

EXAMPLE 24

2-[5-(O-isoureido)pentylamino]-5-(6-methoxy-3-pyridylmethyl)-4-pyrimidone.

EXAMPLE 25

2-[5-(O-isoureido)pentylamino]-5-(2-methoxy-4-pyridylmethyl)-4-pyrimidone.

EXAMPLE 26

2-[5-(O-isoureido)pentylamino]-5-(4-methoxy-2-pyridylmethyl)-4-pyrimidone (iv) Heating the above 2-[5-(O-isoureido)pentylamino]-4-pyrimidones with 2N hydrogen chloride in methanol gives

EXAMPLE 27

2-[5-(O-isoureido)pentylamino]-5-(6-hydroxy-3-pyridylmethyl)-4-pyrimidone.

EXAMPLE 28

2-[5-(O-isoureido)pentylamino]-5-(2-hydroxy-4-pyridylmethyl)-4-pyrimidone.

EXAMPLE 29

2-[5-(O-isoureido)pentylamino]-5-(4-hydroxy-2-pyridylmethyl)-4-pyrimidone.

EXAMPLE 30

(i) Reaction of 2-nitroamino-5-(6-methyl-3-pyridylmethyl)-4-pyrimidone with 3-chloroperoxybenzoic acid in acetic acid gave 2-nitroamino-5-(N-oxo-6-methyl-3-pyridylmethyl)-4-pyrimidone, m.p. 232° (decomp.) which is reacted with 5-aminopentanol to give 2-(5-hydroxypentylamino)-5-(N-oxo-6-methyl-3-pyridylmethyl)-4-pyrimidone.

(ii) Reaction of the latter compound with cyanamide and hydrogen chloride gives 2-[5-(O-isoureido)pentylamino]-5-(N-oxo-6-methyl-3-pyridylmethyl)-4-pyrimidone.

EXAMPLES 31 TO 41

Reaction of the 2-(ω-hydroxyalkylamino)-4-pyrimidone derivatives described in Examples 17 to 23 and 30 with thionyl chloride and subsequent reaction with thiourea gives

EXAMPLE 31

2-[3-(S-isothioureido)propylamino]-5-(6-methyl-3-pyridylmethyl)-4-pyrimidone.

EXAMPLE 32

2-[7-(S-isothioureido)heptylamino]-5-(6-methyl-3-pyridylmethyl)-4-pyrimidone.

EXAMPLE 33

2-[8-(S-isothioureido)octylamino]-5-(6-methyl-3-pyridylmethyl)-4-pyrimidone.

EXAMPLE 34

2-[5-(S-isothioureido)pentylamino]-6-methyl-5-(3-pyridylmethyl)-4-pyrimidone.

EXAMPLE 35

2-[5-(S-isothioureido)pentylamino]-5-(1-3-pyridyl)ethyl)-4-pyrimidone.

EXAMPLE 36

2-[5-(S-isothioureido)pentylamino]-5-(6-methyl-3-pyridylmethyl)-pyrimid-4-thione.

EXAMPLE 37

2-[5-(S-isothioureido)pentylamino]-5-(5,6-dimethyl-3-pyridylmethyl)-4-pyrimidone.

EXAMPLE 38

2-[5-(S-isothioureido)pentylamino]-5-(6-methoxy-3-pyridylmethyl)-4-pyrimidone.

EXAMPLE 39

2-[5-(S-isothioureido)pentylamino]-5-(2-methoxy-4-pyridylmethyl)-4-pyrimidone.

EXAMPLE 40

2-[5-(S-isothioureido)pentylamino]-5-(4-methoxy-2-pyridylmethyl)-4-pyrimidone.

EXAMPLE 41

2-[5-(S-isothioureido)pentylamino]-5-(N-oxo-6-methyl-3-pyridylmethyl)-4-pyrimidone.

EXAMPLES 42 TO 44

Heating the 5-(methoxypyridylmethyl)-4-pyrimidones of Examples 37 to 39 with 2N hydrogen chloride in methanol gives

EXAMPLE 42

2-[5-(S-isothioureido)pentylamino]-5-(6-hydroxy-3-pyridylmethyl)-4-pyrimidone.

EXAMPLE 43

2-[5-(S-isothioureido)pentylamino]-5-(2-hydroxy-4-pyridylmethyl)-4-pyrimidone.

EXAMPLE 44

2-[5-(S-isothioureido)pentylamino]-5-(4-hydroxy-2-pyridylmethyl-4-pyrimidone.

EXAMPLE 45

Reaction of 5-aminopentanol with (a) 5-(1-naphthylmethyl)-2-methylthio-4-pyrimidone
(b) 5-(3-quinolylmethyl)-2-methylthio-4-pyrimidone gives the corresponding 2-(5-hydroxypentylamino)-4-pyrimidones which are reacted with cyanamide and hydrogen chloride to give
(a) 2-[5-(O-isoureido)pentylamino]-5-(1-naphthylmethyl)-4-pyrimidone
(b) 2-[5-(O-isoureido)pentylamino]-5-(3-quinolylmethyl)-4-pyrimidone

EXAMPLE 46

Reaction of 5-aminopentanol with (a) 5-(2-pyridylmethyl)-2-methylthio-4-pyrimidone
(b) 5-(4-pyridylmethyl)-2-methylthio-4-pyrimidone
(c) 5-(2-thienylmethyl)-2-methylthio-4-pyrimidone
(d) 5-(4-methylbenzyl)-2-methylthio-4-pyrimidone
(e) 5-(3,4,5-trimethoxybenzyl)-2-methylthio-4-pyrimidone
(f) 5-(4-chlorobenzyl)-2-methylthio-4-pyrimidone
(g) 5-(2-chlorobenzyl)-2-methylthio-4-pyrimidone
(h) 5-(3,4-dichlorobenzyl)-2-methylthio-4-pyrimidone
gives the corresponding 2-(5-hydroxypentylamino)-4-pyrimidone which are reacted with cyanamide and hydrogen chloride to give
(a) 2-[5-(O-isoureido)pentylamino]-5-(2-pyridylmethyl)-4-pyrimidone
(b) 2-[5-(O-isoureido)pentylamino]-5-(4-pyridylmethyl)-4-pyrimidone
(c) 2-[5-(O-isoureido)pentylamino]-5-(2-thienylmethyl)-4-pyrimidone
(d) 2-[5-(O-isoureido)pentylamino]-5-(4-methylbenzyl)-4-pyrimidone
(e) 2-[5-(O-isoureido)pentylamino]-5-(3,4,5-trimethoxybenzyl)-4-pyrimidone
(f) 2-[5-(O-isoureido)pentylamino]-5-(4-chlorobenzyl)-4-pyrimidone
(g) 2-[5-(O-isoureido)pentylamino]-5-(2-chlorobenzyl)-4-pyrimidone
(h) 2-[5-(O-isoureido)pentylamino]-5-(3,4-dichlorobenzyl)-4-pyrimidone

EXAMPLE 47

Reaction of 5-aminopentanol with
(a) 5-benzyloxy-2-methylthio-4-pyrimidone
(b) 5-(2-(4-methoxybenzyloxy)ethyl)-2-methylthio-4-pyrimidone
(c) 5-(2-(4-methoxybenzylthio)ethyl)-2-methylthio-4-pyrimidone
(d) 5-(2-(3-pyridylmethylthio)ethyl)-2-methylthio-4-pyrimidone
(e) 5-(2-phenylethyl)-2-methylthio-4-pyrimidone
(f) 5-(2-phenylethyl)-6-methyl-2-methylthio-4-pyrimidone
(g) 5-(4-phenylbutyl)-2-methylthio-4-pyrimidone gives the corresponding 2-(5-hydroxypentylamino)-4-pyrimidones which are reacted with cyanamide and hydrogen chloride or S-methylisothiourea and sodium hydride to give
(a) 2-[5-(O-isoureido)pentylamino]-5-benzyloxy-4-pyrimidone
(b) 2-[5-(O-isoureido)pentylamino]-5-(2-(4-methoxybenzyloxy)ethyl)-4-pyrimidone
(c) 2-[5-(O-isoureido)pentylamino]-5-(2-(4-methoxybenzylthio)ethyl)-4-pyrimidone
(d) 2-[5-(O-isoureido)pentylamino]-5-(2-(3-pyridylmethylthio)ethyl)-4-pyrimidone
(e) 2-[5-(O-isoureido)pentylamino]-5-(2-phenylethyl)-4-pyrimidone
(f) 2-[5-(O-isoureido)-pentylamino]-5-(2-phenylethyl)-6-methyl-4-pyrimidone
(g) 2-[5-(O-isoureido)pentylamino]-5-(4-phenylbutyl)-4-pyrimidone

EXAMPLE 48

Substitution of the following 3-(heteroaryl)propionates:
(a) ethyl 3-(2-methoxy-3-pyridyl)propionate
(b) ethyl 3-(4,6-dimethoxy-3-pyridyl)propionate
(c) ethyl 3-(2,6-dimethoxy-4-pyridyl)propionate
(d) ethyl 3-(4,5-dimethoxy-2-pyridyl)propionate
(e) ethyl 3-(5-hydroxy-2-pyridyl)-propionate
(f) ethyl 3-(4-hydroxy-2-pyrimidyl)propionate
(g) ethyl 3-(4-hydroxy-5-methoxy-2-pyridyl)propionate
(h) ethyl 3-(4-hydroxy-3-methoxy-2-pyridyl)propionate
(i) ethyl 3-(4,5-dimethyl-2-thienyl)propionate
(j) ethyl 3-(6-amino-3-pyridyl)propionate
(k) ethyl 3-(4-isoquinolyl)propionate
(l) ethyl 3-(3-chloro-2-pyridyl)propionate
for ethyl 3-(6-methyl-3-pyridyl)propionate in the procedure of Example 5(i)-(iii) gives the corresponding 2-[5-(O-isoureido)pentylamino]-5-(heteroarylmethyl)-4-pyrimidones.

The starting materials may be prepared by condensing the corresponding heterocyclic carboxaldehyde with (i) malonic acid, and hydrogenating and esterifying the products or (ii) diethyl malonate, reducing the product with sodium borohydride followed by hydrolysis, monodecarboxylation and esterification, or by reacting a halomethylheterocyclic derivatives with sodium and diethyl malonate, and hydrolysing, monodecarboxylating and esterifying the product.

EXAMPLE 49

Substitution of the following 3-arylpropionates:
(a) ethyl 3-(6-(2,3-dihydro-1,4-benzodioxinyl)propionate
(b) ethyl 3-(3-benzyloxyphenyl)propionate
(c) ethyl 3-(3-methoxymethoxyphenyl)propionate (prepared by reacting ethyl 3-(3-hydroxyphenyl)propionate with dimethoxymethane)
(d) ethyl 3-(3-trifluoromethylphenyl)propionate
(e) ethyl 3-(4-dimethylaminophenyl)propionate
(f) ethyl 3-(4-phenoxyphenyl)propionate
(g) ethyl 3-(4-(4-chlorophenoxy)phenyl)propionate
(h) ethyl 3-(4-(4-methoxyphenoxy)phenyl)propionate
(i) ethyl 3-(4-biphenylyl)propionate
(j) ethyl 3-(4'-chloro-4-biphenylyl)propionate
(k) ethyl 3-(4'-methoxy-4-biphenylyl)propionate
for ethyl 3-(6-methyl-3-pyridyl)propionate in the procedure of Example 5(i)-(iii) gives the corresponding 2-[5-(O-isoureido)pentylamino]-5-(arylmethyl)-4-pyrimidones.

Treatment of the product from (c) with hydrochloric acid gives the 5-(3-hydroxybenzyl)pyrimidone.

EXAMPLE 50

Substitution of the following 3-(heteroaryl)propionates:
(a) ethyl 3-(2-furyl)propionate
(b) ethyl 3-(2-thiazolyl)propionate
(c) ethyl 3-(5-oxazolyl)propionate
(d) ethyl 3-(3-isothiazolyl)propionate
(e) ethyl 3-(2-pyrimidyl)propionate
(f) ethyl 3-(5-pyrimidyl)propionate
(g) ethyl 3-(2-pyrazyl)propionate
(h) ethyl 3-(4-pyridazyl)propionate
(i) ethyl 3-(2-(5-amino-1,3,4-thiadiazolyl)propionate
(j) ethyl 3-(1-isoquinolyl)propionate
(k) ethyl 3-(1,3-dioxolo[4,5-C]-pyridyl)propionate
(l) ethyl 3-(2-benzimidazolyl)propionate
(m) ethyl 3-(2-benzthiazolyl)propionate
for ethyl 3-(6-methyl-3-pyridyl)propionate in the procedure of Example 5(i)-(iii) gives the corresponding 5-(heteroarylmethyl)-4-pyrimidones.

The starting materials can be prepared as described in Example 48.

EXAMPLE 51

Substitution of
(a) ethyl octanoate
(b) ethyl 3-cyclohexylpropionate
for ethyl 3-(6-methyl-3-pyridyl)propionate in the procedure of Example 5(i)-(iii) gives (i) (a) 5-hexyl-2-thiouracil m.p. 169.5°–172° (from aqueous ethanol)
(b) 5-cyclohexylmethyl-2-thiouracil m.p. 210°–211° (from ethanol)
(ii) (a) 5-hexyl-2-methylthio-4-pyrimidone m.p. 116°–117.5° (from aqueous ethanol)
(b) 5-cyclohexylmethyl-2-methylthio-4-pyrimidone m.p. 187°–188° (from acetic acid)
(iii) (a) 2-[5-(O-isoureido)pentylamino]-3-hexyl-4-pyrimidone
(b) 2-[5-(O-isoureido)pentylamino]-5-cyclohexylmethyl-4-pyrimidone.

EXAMPLE 52

A pharmaceutical compositon is prepared from the following ingredients:

| | |
|---|---|
| 2-[5-(O—isoureido)pentylamino]-5-(3-pyridylmethyl)-pyrimidone | 150 mg |
| Sucrose | 75 mg |
| Starch | 25 mg |
| Talc | 5 mg |
| Stearic acid | 2 mg |

The ingredients are screened, mixed and filled into a hard gelatin capsule.

Similarly the other compounds of Structure 1 can be formulated into pharmaceutical compositions by the procedure of Example 52. These pharmaceutical compositions are administered to a subject within the dose ranged given hereabove to block histamine $H_2$- and $H_1$-receptors and to alleviate acute inflammation.

EXAMPLE 53

Preparation of a pharmaceutical composition for topical administration containing

| | | % w/w |
|---|---|---|
| A | Stearyl alcohol | 15.0 |
| | Beeswax | 8.0 |
| | Sorbitan monooleate | 1.25 |
| | Polyoxyethylene sorbitan monooleate | 3.75 |
| | The product of any one of Examples 1 to 51 | 1.0 |
| | Sorbitol solution BP | 7.5 |

| | | % w/w |
|---|---|---|
| B | Citric Acid | 0.2 |
| | Sodium Citrate | 0.05 |
| | Methylparaben | 0.18 |
| | Propylparaben | 0.02 |
| | Water | to 100 |

A mixture of the ingredients A is heated to 72°, added with stirring to a mixture of the ingredients B at 70°, and the stirring is continued until a cream is formed.

EXAMPLE 54

An injectable pharmaceutical composition is prepared by dissolving 2-[5-(S-isothioureido)pentylamino]-5-(3-pyridylmethyl)-4-pyrimidone trihydrochloride (100 g) in sterile water (2 liters). From it are prepared ampoules containing 100 mg of active ingredient.

We claim:
1. A compound of the formula

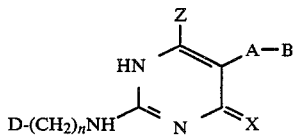

where D is chlorine, bromine, iodine, toluene-p-sulphonyloxy or methanesulphonyloxy; n is from 3 to 8; X is oxygen or sulphur; Z is hydrogen or lower alkyl; A is straight or branched $C_1$–$C_5$ alkylene or —$(CH_2)_pW(CH_2)_q$— where W is oxygen or sulphur and the sum of p and q is 1 to 4; and B is methyl, $C_3$–$C_6$ cycloalkyl, a heteroaryl group selected from pyridyl, N-oxopyridyl, furyl, thienyl, thiazolyl, oxazolyl, isothiazolyl, imidazolyl, pyrimidyl, pyrazyl, pyridazyl, thiadiazolyl, quinolyl, isoquinolyl, 5,6,7,8-tetrahydroquinolyl, 1,3-dioxolopyridyl, benzimidazolyl and benzthiazolyl, said heteroaryl group being optionally substituted by one or more lower alkyl, lower alkoxy, halo, hydroxy or amino groups or B is a naphthyl, 5- or 6-(2,3-dihydro-1,4-benzodioxinyl) or 4- or 5-(1,3-benzodioxolyl) group, or a phenyl group optionally substituted with one, two or three lower alkoxy or one or two lower alkyl, halogen, phenyl(lower alkoxy), hydroxy, lower alkoxy-lower alkoxy, trifluoromethyl, di(lower alkyl)amino, phenoxy, halophenoxy, lower alkoxyphenoxy, phenyl, halophenyl or lower alkoxyphenyl group, or, provided A is methylene, B can be hydrogen, in the form of the free base or a pharmaceutically acceptable acid addition salt thereof.

2. A compound according to claim 1 in which D is chlorine, bromine or iodine.

* * * * *